United States Patent
Sasayama (10) Patent No.: US 7,471,763 B2
(45) Date of Patent: Dec. 30, 2008

(54) FLUORESCENT X-RAY ANALYSIS APPARATUS

(75) Inventor: Norio Sasayama, Chiba (JP)

(73) Assignee: SII Nano Technology Inc., Chiba (JP)

( * ) Notice: Subject to any disclaimer, the term of this patent is extended or adjusted under 35 U.S.C. 154(b) by 0 days.

(21) Appl. No.: 11/805,664

(22) Filed: May 24, 2007

(65) Prior Publication Data
US 2007/0280414 A1 Dec. 6, 2007

(30) Foreign Application Priority Data
Jun. 6, 2006 (JP) .............................. 2006-156821

(51) Int. Cl.
*G01N 23/223* (2006.01)
(52) U.S. Cl. .......................................... 378/45; 378/44
(58) Field of Classification Search .............. 378/44–50
See application file for complete search history.

(56) References Cited

U.S. PATENT DOCUMENTS 3,944,822 A * 3/1976 Dzubay ....................... 378/45
6,049,589 A * 4/2000 Sipila ......................... 378/143

FOREIGN PATENT DOCUMENTS

EP 0 887 639 A1 12/1998
SU 1045094 A 9/1983

OTHER PUBLICATIONS

Search Report issued Oct. 11, 2007 in European patent application No. 07252275.8.

* cited by examiner

*Primary Examiner*—Hoon Song
(74) *Attorney, Agent, or Firm*—Brinks Hofer Gilson & Lione (57) ABSTRACT

To provide a fluorescent X-ray analysis apparatus using a polarization for effectively measuring a minute portion of a sample surface without a necessary to prepare many kinds of secondary targets. A fluorescent X-ray analysis apparatus according to the present invention includes an X-ray tube for generating an X-ray; a sample support portion for supporting a sample receiving the X-ray; a polarization filter for receiving an X-ray to be generated from the sample receiving the X-ray; and a detector for detecting the X-ray from the polarization filter. Then, the X-ray tube, the sample, the polarization filter, and the detector are arranged so that three light paths, namely, a light path from the X-ray tube to the sample, a light path from the sample to the polarization filter, and a light path from the polarization filter to the detector intersect with each other at 90 degrees.

24 Claims, 9 Drawing Sheets

FLUORESCENT X-RAY ANALYSIS APPARATUS

This application claims priority under 35 U.S.C. §119 to Japanese Patent Application No. JP2006-156821 filed Jun. 6, 2006, the entire content of which is hereby incorporated by reference.

BACKGROUND OF THE INVENTION

1. Field of the Invention

The present invention relates to a fluorescent X-ray analysis apparatus having means for decreasing a background component of an obtained spectrum by using a polarized light of an X-ray mounted thereon.

2. Description of the Related Art

In a fluorescent X-ray analysis, it is important to detect a fluorescent X-ray generated in a sample, however, even if an X-ray generated in an X-ray tube is detected, the detected X-ray only becomes a background component, which is not necessary for analysis. Therefore, in order to increase an intensity rate (an S/N rate) of a necessary fluorescent X-ray component for an unnecessary X-ray, some methods are employed. Among them, there is a method to use a polarized light of the X-ray. According to a fluorescent X-ray analysis apparatus using a conventional polarized light, an X-ray tube, a secondary target, a sample, and a detector are arranged so as to constitute a polarization optics, which is referred to as a Cartesian arrangement. On the basis of this arrangement, it is possible to prevent that an X-ray generated in the X-ray tube attains to the detector.

Figure 2:
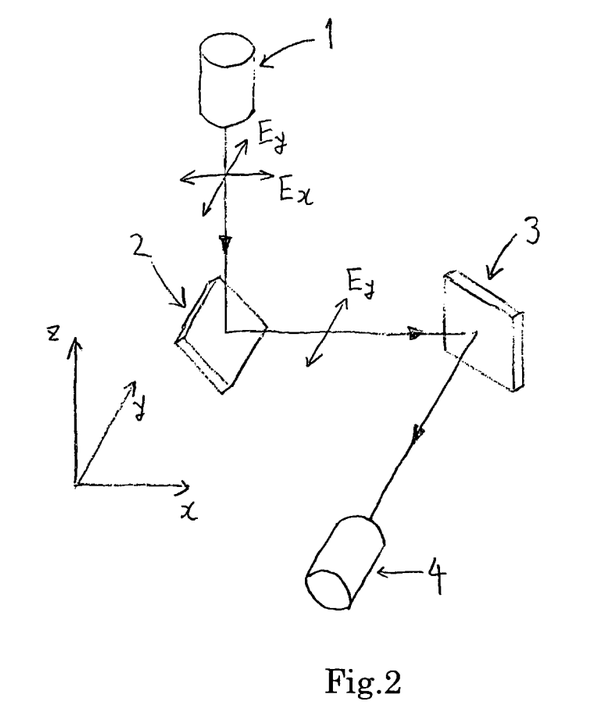
FIG. 2 is a view showing a Cartesian arrangement of a conventional fluorescent X-ray analysis apparatus.

Specifically, in a light path of the X-ray passing through the X-ray tube, the secondary target, the sample, and the detector, the following physics phenomenon is generated. This phenomenon will be described along the X-ray light path with reference to FIG. 2. In FIG. 2, directions of x, y, and z; arrangement of components; and a polarization component emitted from the X-ray tube are illustrated, which will be described below.

(1) The X-ray emitted from an X-ray tube 1 is generated when an electron ray is irradiated to a tube target inside of the tube, and the X-ray includes polarization components in two directions, namely, an x direction and a y direction.

(2) In the secondary target, two kinds of phenomena, namely, a phenomenon such that the X-ray emitted from the X-ray tube 1 is scattered and a phenomenon such that a fluorescent X-ray from an element in a secondary target 2, which is excited by the X-ray emitted from the X-ray tube 1, is emitted occur. In the Cartesian arrangement, a sample 3 is disposed in a direction that a scatter angle becomes 90 degrees, so that the polarization component in the x direction is not included in the X-ray which is scattered in the direction of the sample 3. This phenomenon is generated because a refractive index of the secondary target for the X-ray is slightly smaller than the refractive index of air. In addition, the fluorescent X-ray emitted from the element in the secondary target includes the polarization components in two directions, namely, an y direction and a z direction.

(3) In the sample, two kinds of phenomena, namely, a phenomenon such that the scattered X-ray and the fluorescent X-ray emitted from the secondary target 2 are scattered and a phenomenon such that a fluorescent X-ray from the element in the sample 3, which is excited by the scattered X-ray and the fluorescent X-ray emitted from the secondary target 2, is emitted occur. In the Cartesian arrangement, a detector 4 is disposed in a direction that a scatter angle becomes 90 degrees and the direction from the sample 3 to the detector 4 becomes 90 degrees for the direction from the X-ray tube 1 to the secondary target 2, so that the polarization component in the y direction is not included in the X-ray which is scattered in the direction of the detector 4. This phenomenon is generated because a refractive index of the sample 3 for the X-ray is slightly smaller than the refractive index of air. In addition, the fluorescent X-ray emitted from the element in the sample 3 includes the polarization components in two directions, namely, a z direction and an x direction.

(4) The X-ray attaining to the detector 4 only has a polarization component in the z direction of the fluorescent X-ray generated in the secondary target and a polarization component in the z direction and the x direction of the fluorescent X-ray generated in the sample. In the X-ray emitted from the X-ray tube 1, the both components in x and y cannot attain to the detector 4 as a result of scatter twice in the secondary target 2 and the sample 3.

On the basis of the above-described physics phenomenon, the fluorescent X-rays generated in the secondary target and the sample 3 only attain to the detector 4, and a measurement result having very little background can be obtained (for example, refer to U.S. Pat. No. 3,944,822 (see claim 3)).

According to a conventional apparatus, the element in the sample is excited by the scattered X-ray and the fluorescent X-ray emitted from the secondary target. In addition, it is necessary to select a secondary target material so that an energy of the fluorescent X-ray generated in the secondary target is slightly larger than an excitation energy of a sample element so as to increase an excitation efficiency by means of the fluorescent X-ray. On the contrary, in the condition that the energy of the fluorescent X-ray generated in the secondary target and the excitation energy of the sample element are separated or the like, the excitation efficiency of the sample element is remarkably deteriorated. In order to avoid such a condition, preparing many kinds of the secondary targets in response to the sample element, the secondary targets are necessarily used being changed over.

In addition, both of the scattered X-ray and the fluorescent X-ray emitted from the secondary target are diffused in many directions. It is necessary to irradiate most of the X-rays to be diffused to the sample and this involves a problem such that the X-ray irradiation amount is remarkably decreased if a collimator is used in order to measure a minute portion of a sample surface. In the case of focusing the X-rays on the minute portion of the sample surface by using a lens for an X-ray in place of the collimator, there is a problem such that a condition of polarization optics is not met.

SUMMARY OF THE INVENTION

The present invention has been made taking the foregoing problems into consideration and an object thereof is to make measurement of a minute portion of a sample surface easy without necessary of preparation of many kinds of secondary targets.

In order to attain the above described problems, a fluorescent X-ray analysis apparatus according to the present invention may employ a polarization optics, in which the order of the secondary target is contrary to the order of the sample. In this case, it is not appropriate to name a secondary target, so that this is named as a polarization filter. Not many kinds but a kind or a few kinds of polarization filters are prepared. In other words, the fluorescent X-ray analysis apparatus according to the present invention may comprise an X-ray tube for generating an X-ray; a sample support portion for supporting a sample receiving the X-ray; a polarization filter for receiving an X-ray to be generated from the sample receiving the X-ray; and a detector for detecting the X-ray from the polarization filter. Then, the X-ray tube, the sample support portion, the polarization filter, and the detector are arranged so that three light paths, namely, a light path from the X-ray tube to the sample, a light path from the sample to the polarization filter, and a light path from the polarization filter to the detector intersect with each other at 90 degrees.

In addition, as the above-described polarization filter, using a curved-shaped one, it is preferable that the polarization filter is arranged so that most of the X-rays to be diffused from the sample is effective for most of the X-rays to be diffused from the sample.

In addition, it is preferable that, as the shape of the polarization filter, the surface is curved so as to be along a circumference of one circle, the sample, and the detector, or a detector collimator are arranged so as to be separated 180 degrees on the circumference, and the X-ray tube is disposed so that the direction of the X-ray from the X-ray tube toward the sample is vertical to the surface made by the circle.

In addition, it is preferable that, as a shape of the polarization filter, which is curved so as to be along the circumference, a part of a shape so as to adhere to a columnar surface is used.

In addition, it is preferable that an X-ray generation source of the X-ray tube and the detector or the detector collimator are arranged so as to be separated 180 degrees on a sphere; a plurality of polarization filters curved so as to be along circumferences of plural circles having a smaller diameter than a diameter of the sphere is arranged on the sphere passing through the position of the detector or the position of the detector collimator, and the sample is arranged on the circumference separated from the detector or the detector collimator 180 degrees for the plural circles.

Further, it is preferable that the sample, the X-ray generation source, and the detector or the detector collimator, which are arranged on the circumferences of the above-described plural circles, are aligned so as to be aligned on a circumference of other circle.

Further, it is preferable that, as the polarization filter, a plurality of plain-shaped polarization filters is arranged so that the surfaces of them are located along a circumference of one circle, and the sample and the detector or the detector collimator are arranged so as to be separated 180 degrees on the circumference, whereby the polarization optical system is disposed so that it is effective to many of the X-ray diffused from the sample. In this case, it is preferable that the X-ray tube is disposed so that the direction of the X-ray from the X-ray tube toward the sample is vertical to the surface made by the circle.

In addition, it is preferable that, as how to align a plurality of plain-shaped polarization filters, which are arranged so as to be along the circumference, it is preferable that the plurality of plain-shaped polarization filters is aligned so as to contact a columnar surface.

In addition, it is preferable that an X-ray generation source of the X-ray tube and the detector or the detector collimator are arranged so as to be separated 180 degrees on a sphere; a plurality of plain-shaped polarization filters so as to be along circumferences of plural circles having a smaller diameter than a diameter of the sphere is arranged on the sphere passing through the position of the detector or the position of the detector collimator, and the sample is arranged on the circumference separated from the detector or the detector collimator 180 degrees for the plural circles.

In addition, it is preferable that the sample, the X-ray generation source, and the detector or the detector collimator, which are arranged on the circumferences of the above-described plural circles, are aligned so as to be aligned on a circumference of other circle.

In addition, it is preferable that measurement means for measuring a component after the fluorescent X-ray generated in the sample is Compton-scattered by the polarization filter is mounted.

In addition, it is preferable that the polarization filter is made of a material of a major ingredient, of which atomic number is 14 or less.

In addition, it is preferable that the polarization filter is made of a material of a major ingredient, of which atomic number is 8 or less.

In addition, it is preferable that a lens for an X-ray for focusing the X-rays from the X-ray tube is arranged between the X-ray tube and the sample so as to carry out measurement of a minute portion of a sample surface.

In addition, it is preferable that there is provided a fluorescent X-ray analysis method for arranging an X-ray tube, a sample, a polarization filter, and a detector so that three light paths, namely, an X-ray light path from the X-ray tube to the sample, an X-ray light path from the sample to the polarization filter, and an X-ray light path from the polarization filter to the detector intersect with each other at 90 degrees.

In addition, it is preferable that a component after the fluorescent X-ray generated in the sample is Compton-scattered by the polarization filter is measured.

The present invention has the following effects.

Selection of a kind in response to each sample which is required from the secondary target is not necessary for a polarization filter which is disposed at a rear step of the sample, so that exchange of the polarization filter is not needed. On the condition that the polarization filter is exchanged, only few kinds of polarization filters are required and this can be realized by a simple exchange mechanism. In addition, even when the order of the sample is exchanged with that of the secondary target, the same influence is given to the polarization component of the X-ray from the X-ray tube and the effect to prevent the X-ray from the X-ray tube from attaining to the detector and to decrease the background component is equal to the conventional example.

Then, by making the shape of the polarization filter not into a plane surface but into a curved surface, the effect of the polarization optics can be enhanced. The X-ray scattered and diffused from the sample attains to the polarization filter and a part of the X-ray scattered there attains to the detector, however, all of the X-rays to be detected do not satisfy a scatter angle of 90 degree at the polarization filter. By making the shape of the polarization filter into the curved-surface, a shift width from 90 degrees is made smaller and it is possible to enhance the effect to prevent the X-ray from the X-ray tube from attaining to the detector.

Further, by curving the surface of the polarization filter along a circumference of one circle and arranging the sample, the detector, or the detector collimator so as to be separated at 180 degrees each other on the circumference, measurement efficiency can be further enhanced. In this arrangement, in the X-ray diffused from the X-ray tube and scattered on the sample, a scatter angle toward the detector is always 90 degrees even when the X-ray is scattered next on any part superimposed on the circumference of the polarization filter. By making the polarization filter into a curved shape so as to be along a circumference of one circle, using the X-ray from the sample diffused in a wide range, the measurement efficiency can be enhanced. In this case, by disposing the X-ray tube so that the direction of the X-ray from the sample diffused in a wide range is made vertical to the surface made by the circle, the scatter angle when the X-ray emitted from the X-ray tube is scattered on the sample to be directed to the filter is made to be always 90 degrees and thereby, the Cartesian arrangement condition can be met and thereby, it is possible to prevent the X-ray from the X-ray tube from attaining to the detector.

Further, by making the surface of the polarization filter into a curved shape so as to be attached to the columnar surface, making the shift width from the scatter angle of 90 degrees for the X-ray scattered by the polarization filter on the portion which is shifted in a direction vertical to a surface of a page made by the circle, it is possible to prevent the X-ray from the X-ray tube from attaining to the detector.

In addition, a X-ray generation source of the X-ray tube, the detector, or the detector collimator are arranged so as to be separated at 180 degrees each other on a sphere, a plurality of polarization filters curved so as to be along circumferences of plural circles having a smaller diameter than a diameter of the sphere is arranged on the sphere passing through the position of the detector or the position of the detector collimator, and the sample is arranged on the circumference separated from the detector or the detector collimator 180 degrees for these circles, the measurement efficiency can be further enhanced. This arrangement means that a plurality of polarization filters curved so as to be along the circumference of the above-described one circle and a plurality of samples in response to each polarization filter are arranged for one set of the X-ray tube and the detector. As a result, exciting the sample set on plural position of one X-ray tube while satisfying the Cartesian arrangement condition, the measurement efficiency can be increased plural times.

Further, by aligning the sample, the X-ray generation source, and the detector or the detector collimator, which are arranged on the circumferences of the above-described plural circles, so as to be aligned on a circumference of other circle, the plural circles can be arranged so as not to intersect with each other. Therefore, the constitution of the apparatus can be simplified.

In addition, by arranging a plurality of plain-shaped polarization filters so as to be along a circumference of one circle and arranging the sample and the detector, or the detector collimator so as to be separated at 180 degrees on the circumference, it is possible to enhance the measurement efficiency. In this arrangement, in the X-ray emitted from the X-ray tube and diffused on the sample, a scatter angle toward the detector is always about 90 degrees even when the X-ray is scattered next on any part of the polarization filter. By aligning a plurality of plane-shaped polarization filters so as to be along the circumference, using the X-ray from the sample diffused in a wide range, the measurement efficiency can be enhanced. In this case, by disposing the X-ray tube so that the direction of the X-ray from the X-ray tube toward the sample is vertical to the surface made by the circle, making the scatter angle when the X-ray emitted from the X-ray tube is scattered on the sample to be directed to the polarization filter always 90 degrees, the Cartesian arrangement condition can be met, so that it is possible to prevent the X-ray from the X-ray tube from attaining to the detector.

Further, by aligning a plurality of polarization filters so as to contact the columnar surface, making the shift width from the scatter angle of 90 degrees for the X-ray scattered by the polarization filter on the portion which is shifted in a direction vertical to the surface made by the circle, and thereby, it is possible to prevent the X-ray from the X-ray tube from attaining to the detector.

In addition, a X-ray generation source of the X-ray tube, the detector, or the detector collimator are arranged so as to be separated at 180 degrees each other on a sphere, a plurality of plane-shaped polarization filters aligned so as to be along circumferences of plural circles having a smaller diameter than a diameter of the sphere is arranged on the sphere passing through the position of the detector or the position of the detector collimator, and the sample is arranged on the circumference separated from the detector or the detector collimator 180 degrees for these circles, the measurement efficiency can be further enhanced. This arrangement means that plural sets of a plurality of plane-shaped polarization filters aligned so as to be along the circumference of the above-described one circle and a plurality of samples in response to respective sets of polarization filters are arranged for one set of the X-ray tube and the detector. As a result, exciting the sample set on plural position of one X-ray tube while satisfying the Cartesian arrangement condition, the measurement efficiency can be increased plural times.

Further, by arranging the sample, the X-ray generation source, and the detector or the detector collimator, which are arranged on the circumferences of the above-described plural circles, so as to be aligned on a circumference of other circle, the plural circles can be arranged so as not to intersect with each other. Therefore, the constitution of the apparatus can be simplified.

In addition, by mounting measurement means for measuring a fluorescent X-ray after the X-ray is Compton-scattered by the polarization filter, the measurement efficiency can be enhanced. When the fluorescent X-ray is scattered by the polarization filter, Rayleigh scattering that the X-ray is scattered while keeping the energy and Compton scattering that the X-ray is scattered with small energy lost occur and in this case, depending on a filter material, a phenomenon such that the intensity of Compton scattering is made larger than the intensity of Rayleigth scattering dozens of times has been found, so that the measurement efficiency can be enhanced.

Further, the polarization filter is made of a material of a major ingredient, of which atomic number is 14 or less, such as aluminum and quarts ($SiO_2$) or the like, the Compton scattering intensity can be enhanced.

Further, the polarization filter is made of a material of a major ingredient, of which atomic number is 8 or less, such as plastic ($C_xO_yH_z$) or the like, the Compton scattering intensity can be further enhanced.

In addition, according to the fluorescent X-ray analysis apparatus using a normal polarization, by exchanging the order of the sample with that of the secondary target, it is possible to easily response to analysis of a minute portion. Here, a lens for the X-ray is arranged between the X-ray tube and the sample and the X-ray in the light path has both of the polarization conditions in two directions. Therefore, it is not necessary to save the polarization conditions, so that the lens for the X-ray can be used without a problem and this makes it possible to efficiently analyze the minute portion.

In addition, by arranging the X-ray tube, the sample, the polarization filter, and the detector so that three light paths, namely, the X-ray light path from the X-ray tube toward the sample, the X-ray light path from the sample toward the polarization filter, and the X-ray light path from the polarization filter toward the detector intersect with each other at 90 degrees, an analysis method required to prepare only a few kinds of polarization filters while keeping the effect of the polarization optics so as not to prevent the X-ray emitted from the X-ray tube from attaining to the detector can be realized.

Further, by measuring the component after the X-ray is Compton-scattered by the above-described polarization filter, the analysis method to enhance the measurement effect can be realized.

DETAILED DESCRIPTION OF THE INVENTION

The present invention may comprise an X-ray tube for generating an X-ray; a sample support portion for supporting a sample receiving the X-ray; a polarization filter for receiving an X-ray to be generated from the sample receiving the X-ray; and a detector for detecting the X-ray from the polarization filter; in which, the X-ray tube, the sample support portion, the polarization filter, and the detector are arranged so that three light paths, namely, a light path from the X-ray tube to the sample, a light path from the sample to the polarization filter, and a light path from the polarization filter to the detector intersect with each other at 90 degrees. With reference to the drawings, the embodiments according to the present invention will be described below. However, the following embodiments do not limit the present invention.

First Embodiment

Figure 3:
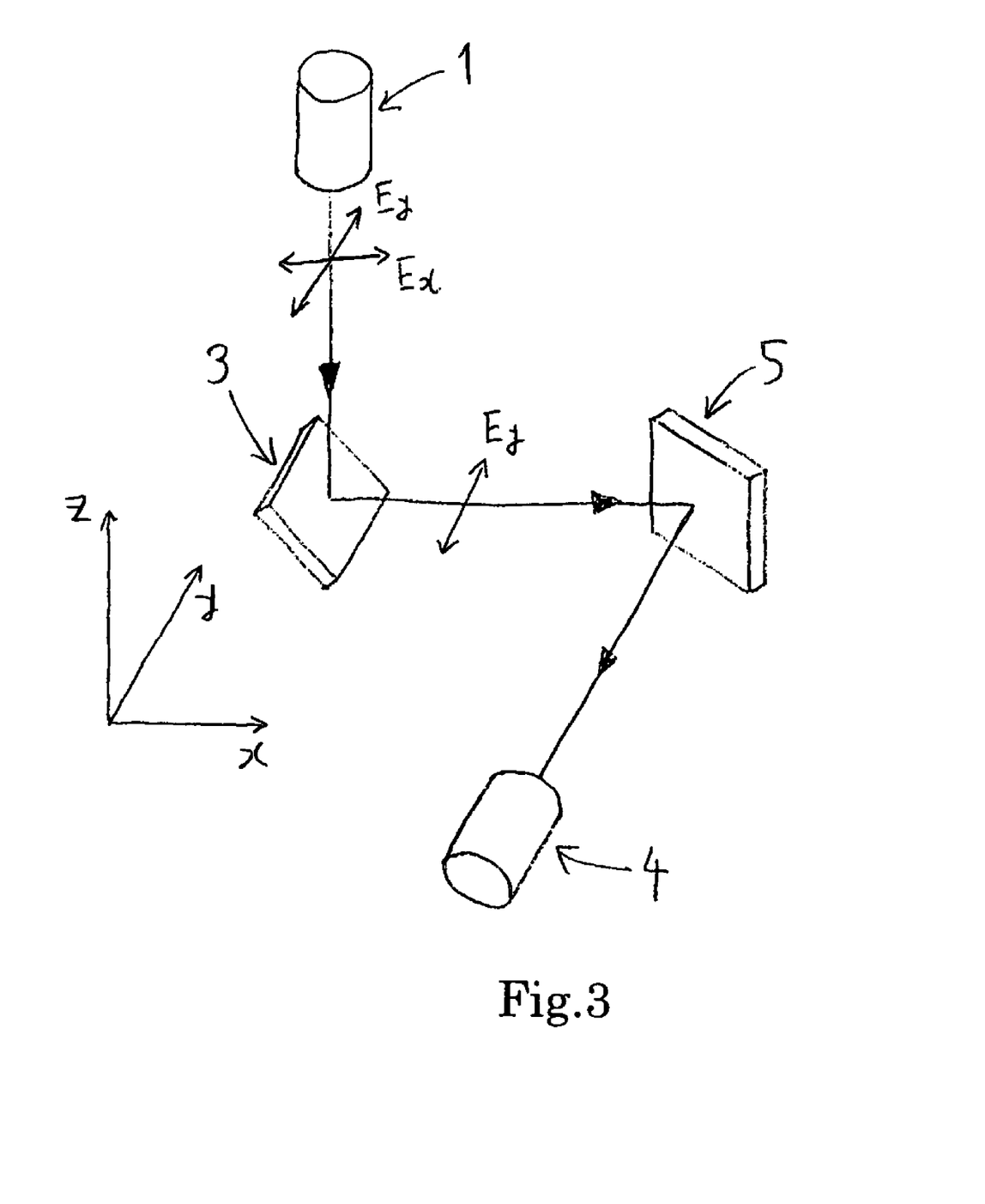
FIG. 3 is a view for showing a first embodiment of a fluorescent X-ray analysis apparatus according to the present invention.

FIG. 3 is a view for showing a first embodiment of a fluorescent X-ray analysis apparatus according to the present invention and shows a positional relation between a X-ray tube 1, a sample 3 supported by a sample support portion (not illustrated), a polarization filter 5, and a detector 4. As compared to the constitution of the apparatus using the conventional polarization shown in FIG. 2, the order of the sample 3 and the order of the secondary target are different, however, the effect for the polarization component of the X-ray emitted from the X-ray tube 1 and the effect to prevent the X-ray from the X-ray tube from attaining to the detector 4 and to decrease the background component are equal to the conventional example.

Second Embodiment

Figure 4:
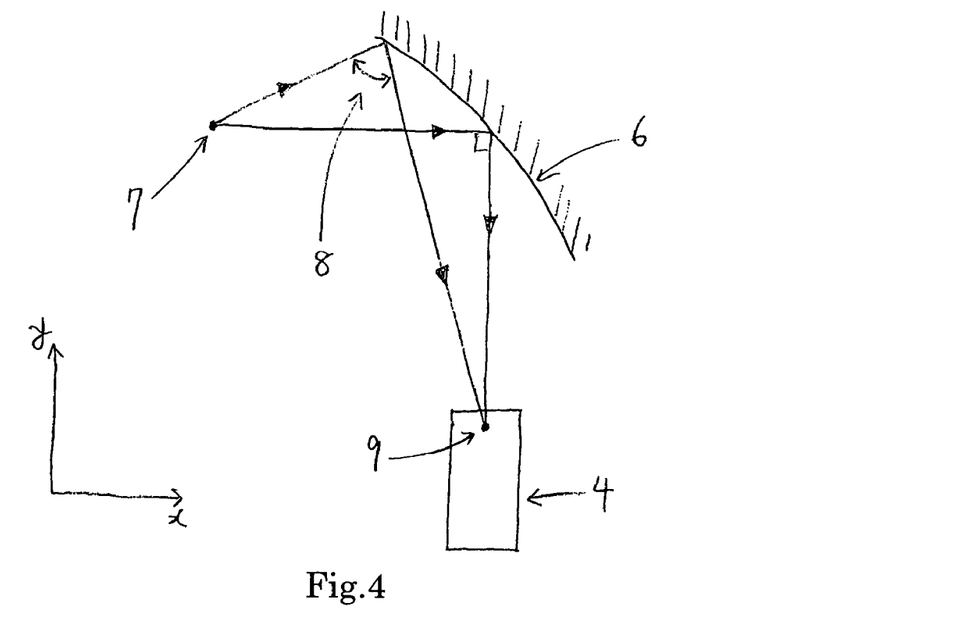
FIG. 4 is a view for showing a second embodiment of a fluorescent X-ray analysis apparatus according to the present invention.
Figure 5:
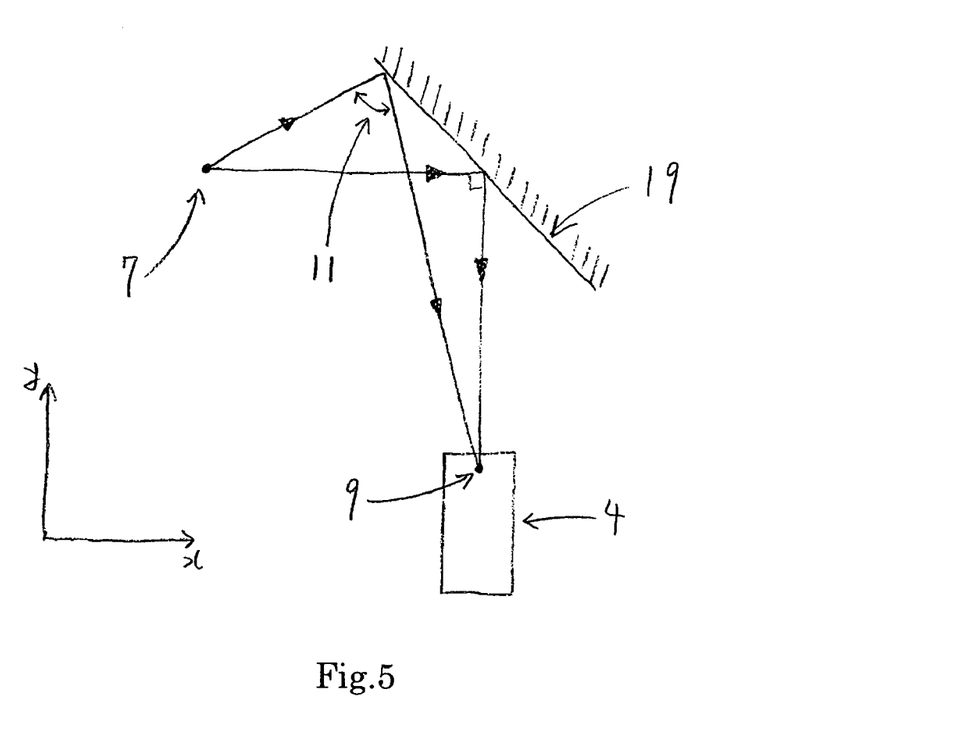
FIG. 5 is a view for showing a comparative example of the first embodiment of a fluorescent X-ray analysis apparatus according to the present invention.

FIG. 4 is a view for showing a second embodiment of a fluorescent X-ray analysis apparatus according to the present invention using a curved-shaped polarization filter 6. In addition, for comparison, an arrangement plan using a plan-shaped polarization filter 19 is shown in FIG. 5. Both of FIG. 4 and FIG. 5 are cross sectional views in the case of seeing arrangement of the components in the same direction (a z direction) as an axis from the X-ray tube toward the sample. In these drawings, the same coordinates as FIG. 3 which is an explanatory view of the first embodiment are used. In addition, clearly showing an X-ray irradiating portion 7 and a detector sensor 9, a scatter angle on the polarization filter is clearly shown. According to an example using the plan-shaped polarization filter 19 shown in FIG. 5, paying attention to a scatter angle of the X-ray, which is emitted from the X-ray irradiating portion 7, is scattered by the polarization filter, and attains to the detector sensor 9, it is found that only a part of the X-rays attaining to the detector satisfies the condition of the scatter angle of 90 degrees. According to the second example of the present invention shown in FIG. 4, it is found that a scatter angle 8 of the X-ray to be scattered on the edge of the polarization filter approaches 90 degrees as compared to a scatter angle 11 shown in FIG. 5. The more this scatter angle approaches 90 degrees, the more effectively it is possible to prevent the X-ray from the X-ray tube from attaining to the detector.

Third Embodiment

Figure 6:
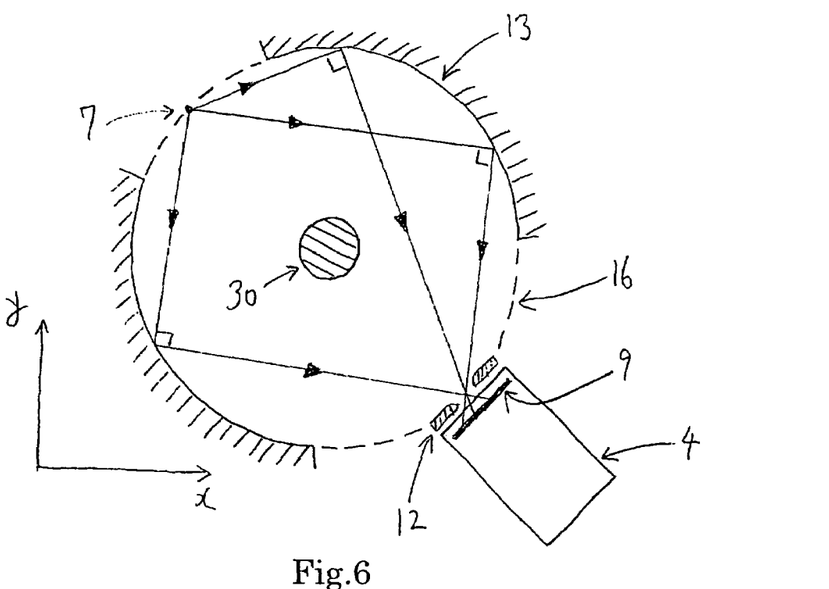
FIG. 6 is a view for showing a third embodiment of a fluorescent X-ray analysis apparatus according to the present invention.

FIG. 6 is a view for showing a third embodiment of a fluorescent X-ray analysis apparatus according to the present invention and shows a manner such that the surface of the polarization filter is curved so as to be along a circumference 16 and the X-ray irradiating portion 7 and the detector collimator 12 on the sample are arranged so as to be separated at 180 degrees on the circumference 16. In FIG. 6, the detector collimator 12 plays a roll to limit the angle of X attaining to the detector, which is played by the detector sensor 9 in FIG. 4, which is an explanatory view of the second embodiment. FIG. 6 shows a manner such that the curved surface of the polarization filter shown in FIG. 4 is arranged so as to be along the circumference 16 and the X-ray irradiating portion 7 and the detector collimator 12 on the sample are arranged on the circumference 16 under the above-described conditions. In addition, in the vicinity of the center of the circumference 16, a shielding body 30 for preventing the X-ray emitted from the X-ray irradiating portion from directly attaining to the detector sensor 9 is disposed.

In such an arrangement, even when the X-ray which is emitted from the X-ray tube and scattered by the X-ray irradiating portion 7 on the sample is scattered next on any part of the part 13 superimposed on the circumference 16 of the polarization filter, it is found that the scatter angle toward the detector collimator 12 is always 90 degrees. As a result, for the increased amount of the total area of the polarization filter as compared to the case of FIG. 4, the X-ray from the sample emitted in a wide range can be used, the scatter angle of 90 degrees can be kept, and measurement with a high efficiency can be realized. In this case, by disposing the X-ray tube so that the direction of the X-ray emitted from the X-ray tube toward the sample becomes vertical to a surface of FIG. 6, the Cartesian arrangement condition can be satisfied with the scatter angle when the X ray emitted from the X-ray tube is scattered by the X-ray irradiating portion 7 on the sample to be directed to the polarization filter always being 90 degrees.

Fourth Embodiment

Figure 1:
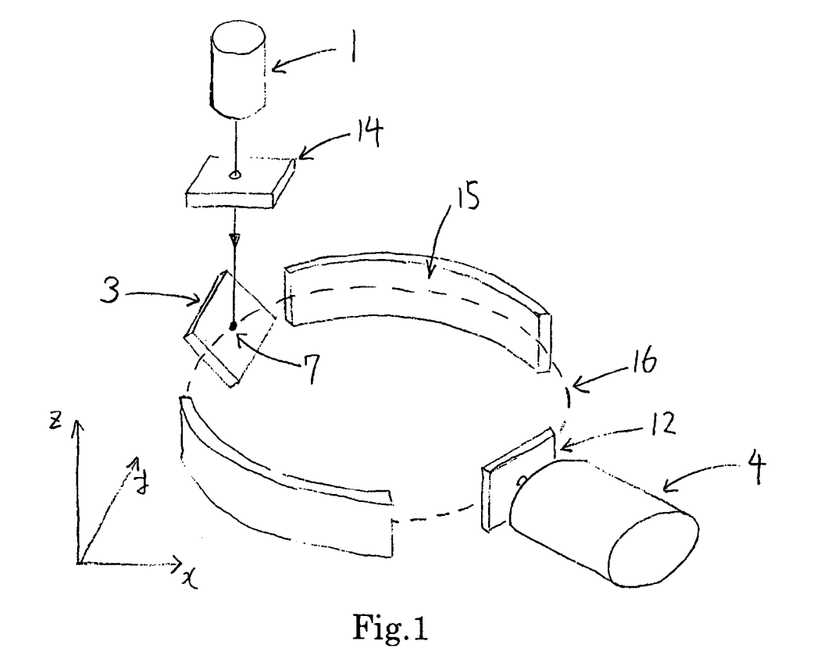
FIG. 1 is a view for showing a fourth embodiment of a fluorescent X-ray analysis apparatus according to the present invention.

FIG. 1 is a view for showing a fourth embodiment of a fluorescent X-ray analysis apparatus according to the present invention and shows a manner that a surface 15 formed so as to adhere to the columnar surface is made into a polarization filter. FIG. 1 is a cubic diagram showing a manner that the constitution in a z direction is added to the explanatory view of the third embodiment shown in FIG. 6. It is also possible to prevent the X-ray scattered by the polarization filter on the portion which is shifted in a z direction (namely, a direction vertical to a surface of a page) from the circumference 16 of FIG. 6 from being largely deviated from the Cartesian arrangement condition, so that the measurement with the high efficiency becomes possible. In FIG. 1, a collimator 14 for controlling a light path so that the X-ray emitted from the X-ray tube only irradiates the limitation range of the sample is also illustrated.

Fifth Embodiment

Figure 7:
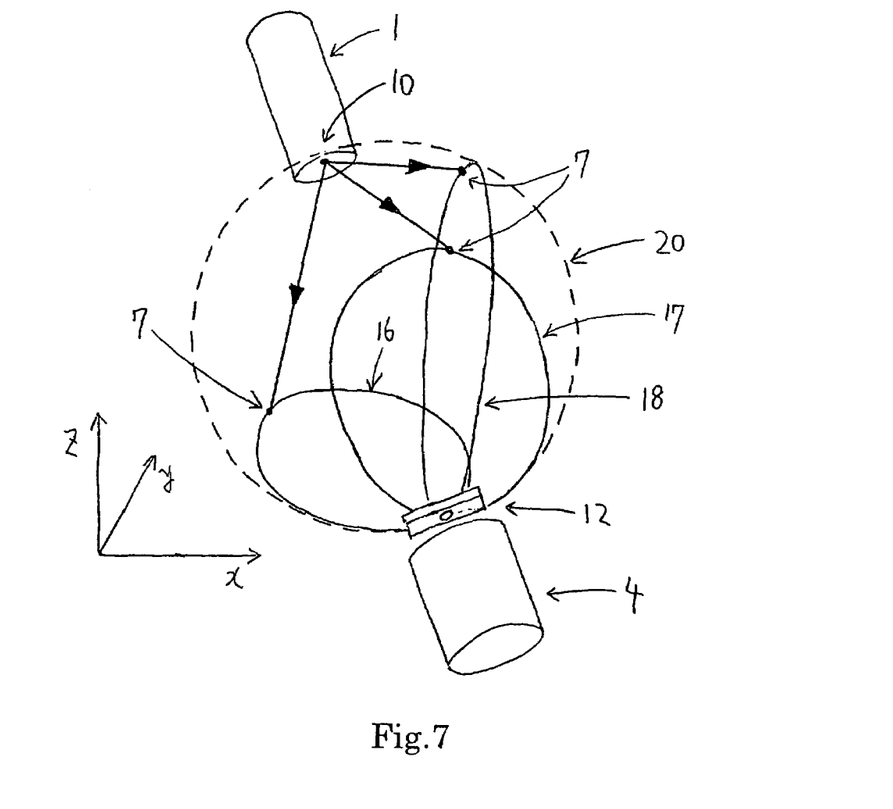
FIG. 7 is a view for showing a fifth embodiment of a fluorescent X-ray analysis apparatus according to the present invention.

FIG. 7 is a view for showing a fifth embodiment of a fluorescent X-ray analysis apparatus according to the present invention and shows a manner that an X-ray generation source 10 of the X-ray tube and the detector collimator 12 are arranged so as to be separated at 180 degrees each other on a sphere 20, a plurality of polarization filters curved so as to be along circumferences 16, 17, and 18 of plural circles having a smaller diameter than a diameter of the sphere is arranged on the sphere passing through the position of the detector collimator 12, and the X-ray irradiating portion 7 is arranged on the circumference separated from the detector collimator 12 at 180 degrees for these circles are arranged. Although FIG. 7 does not show individual polarization filters, the polarization filters formed so as to adhere to the columnar surface as same as FIG. 1, namely, the explanatory view of the fourth embodiment and formed so as to adhere the surface of the sphere 20 are disposed. In this case, the direction of the X-ray toward the X-ray irradiating portion 7, the direction of the X-ray from the X-ray irradiating portion toward the polarization filter, and the direction of the X-ray from the polarization filter toward the detector collimator 12 for each circle intersect with each other at 90 degrees. Therefore, the fifth embodiment can meet the Cartesian arrangement condition.

Sixth Embodiment

Figure 8:
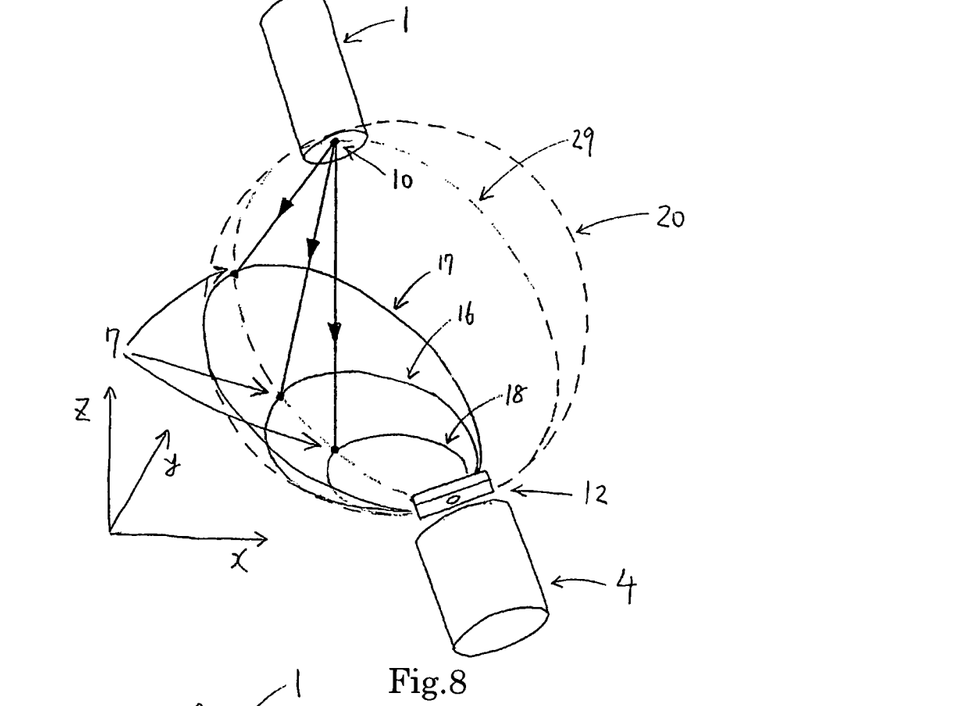
FIG. 8 is a view for showing a sixth embodiment of a fluorescent X-ray analysis apparatus according to the present invention.
Figure 9:
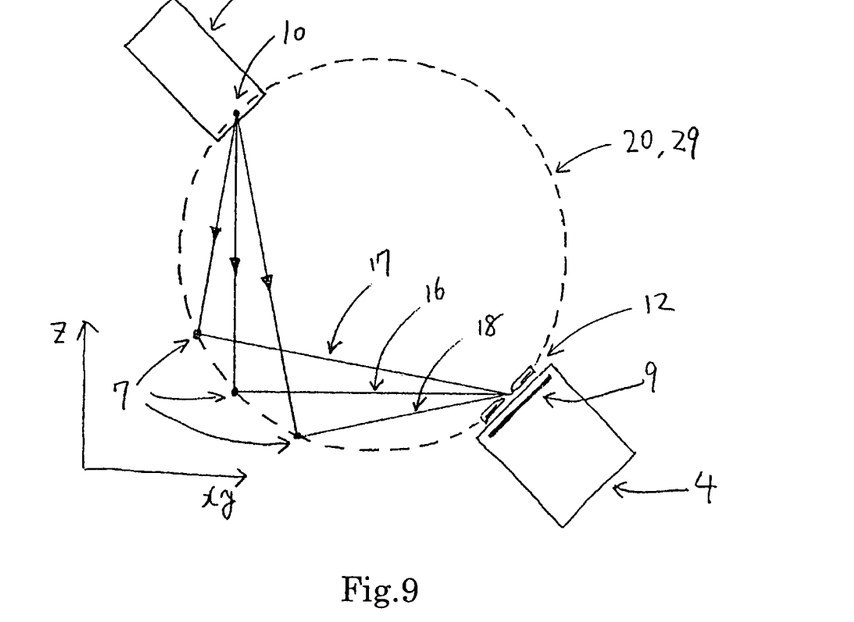
FIG. 9 illustrates the sixth embodiment of the fluorescent X-ray analysis apparatus according to the present invention shown in FIG. 8 in a planar manner.

FIG. 8 is a view for showing a sixth embodiment of a fluorescent X-ray analysis apparatus according to the present invention and shows a manner that a plurality of X-ray irradiating portions 7 arranged on the circumferences 16, 17, and 18 of plural circles shown in FIG. 7, namely, an explanatory view of the fifth embodiment, the X-ray generation source 10, and the detector collimator 12 are arranged so as to be aligned on a circumference 29 of other circle. In addition, FIG. 9 illustrates the sixth embodiment of the fluorescent X-ray analysis apparatus according to the present invention and shows a manner that the same arrangement as shown in FIG. 8 is seen from a direction vertical to a surface made by the circumference 29.

Seventh Embodiment

Figure 10:
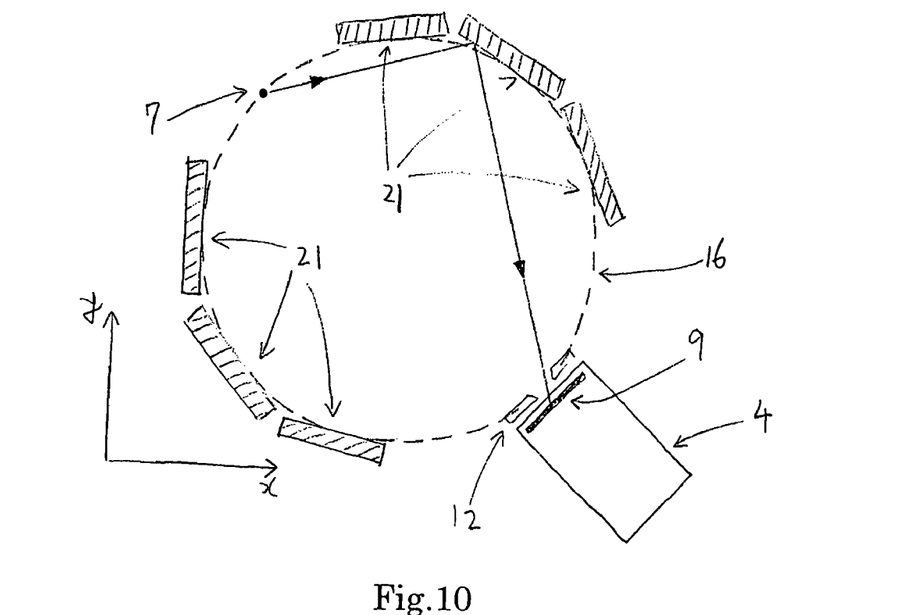
FIG. 10 is a view for showing a seventh embodiment of a fluorescent X-ray analysis apparatus according to the present invention.

FIG. 10 is a view for showing a seventh embodiment of a fluorescent X-ray analysis apparatus according to the present invention and shows a manner that a plurality of plain-shaped polarization filters 21 is aligned so as to be along the circumference 16 and the X-ray irradiating portion 7 and the detector collimator 12 on the sample are arranged so as to be separated at 180 degrees on its circumference 16. FIG. 10 shows a manner that the polarization filter 19 shown in FIG. 5 illustrating the comparative example of the first embodiment is arranged so as to be along the circumference 16 and the X-ray irradiating portion 7 and the detector collimator 12 on the sample are arranged so as to be arranged on its circumference 16.

According to this arrangement, even when the X-ray emitted from the X-ray tube and scattered by the X-ray irradiating portion 7 on the sample is scattered next on any polarization filter, it is found that the scatter angle toward the detector collimator 12 is always 90 degrees. As a result, for the increased amount of the total area of the polarization filter as compared to the case of FIG. 5, the X-ray from the sample emitted in a wide range can be used, the scatter angle of 90 degrees can be kept, and measurement with a high efficiency can be realized. In this case, by disposing the X-ray tube so that the direction of the X-ray emitted from the X-ray tube toward the sample becomes vertical to a surface a page of FIG. 10, the Cartesian arrangement condition can be satisfied with the scatter angle when the X-ray emitted from the X-ray tube is scattered by the X-ray irradiating portion 7 on the sample to be directed to the polarization filter always being 90 degrees.

Eighth Embodiment

Figure 11:
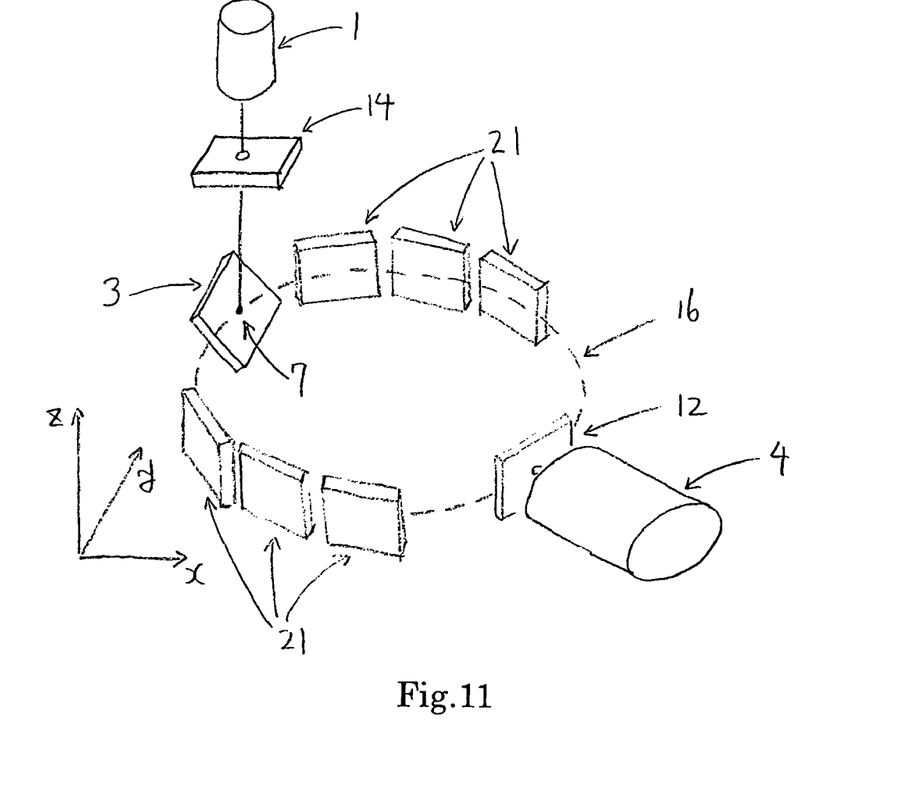
FIG. 11 is a view for showing an eighth embodiment of a fluorescent X-ray analysis apparatus according to the present invention.

FIG. 11 is a view for showing an eighth embodiment of a fluorescent X-ray analysis apparatus according to the present invention and shows a manner that a plurality of plain-shaped polarization filters 21 is aligned so as to be brought into contact with the columnar surface is aligned. FIG. 11 is a cubic diagram showing a manner that the constitution in a z direction (namely, a direction vertical to a surface of a page) is added to FIG. 10, namely, the explanatory view of the seventh embodiment. It is also possible to prevent the X-ray scattered by the polarization filter on the portion which is shifted in a z direction (namely, a direction vertical to a surface of a page) from the circumference 16 of FIG. 10 from being largely deviated from the Cartesian arrangement condition, so that the measurement with the high efficiency becomes possible. In FIG. 11, the collimator 14 for controlling a light path so that the X-ray emitted from the X-ray tube only irradiates the limitation range of the sample is also illustrated.

Ninth Embodiment

Figure 12:
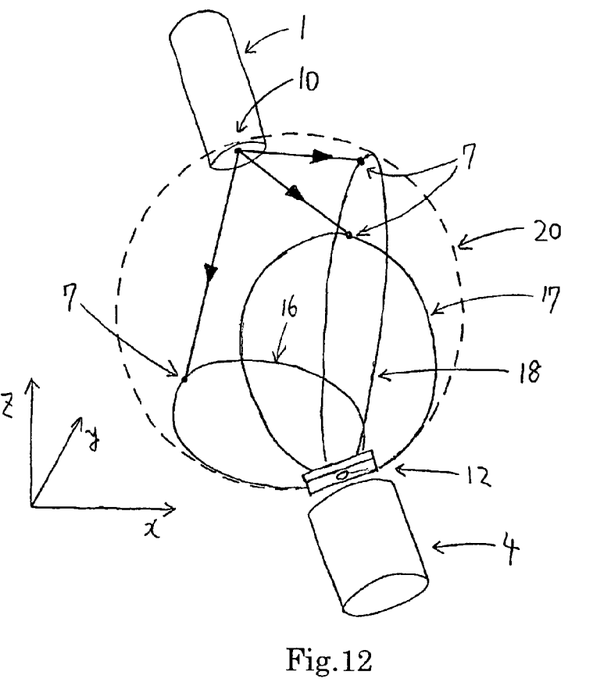
FIG. 12 is a view for showing a ninth embodiment of a fluorescent X-ray analysis apparatus according to the present invention.

FIG. 12 is a view for showing a ninth embodiment of a fluorescent X-ray analysis apparatus according to the present invention and shows a manner that the X-ray generation source 10 of the X-ray tube and the detector collimator 12 are arranged so as to be separated at 180 degrees each other on the sphere 20, a plurality of plain-shaped polarization filters so as to be along the circumferences 16, 17, and 18 of the plural circles having a smaller diameter than a diameter of the sphere is arranged on the sphere 20 passing through the position of the detector collimator 12, and the X-ray irradiating portion 7 is arranged on the circumference separated from the detector collimator 12 at 180 degrees for these circles are arranged. Although FIG. 12 does not show individual polarization filters, the polarization filters formed so as to contact the columnar surface as same as FIG. 11, namely, the explanatory view of the eighth embodiment and formed so as to contact the surface of the sphere 20 are disposed. In this case, the direction of the X-ray toward the X-ray irradiating portion 7, the direction of the X-ray from the X-ray irradiating portion toward the polarization filter, and the direction of the X-ray from the polarization filter toward the detector collimator 12 for each circle intersect with each other at 90 degrees. Therefore, the fifth embodiment can meet the Cartesian arrangement condition. Incidentally, FIG. 12 shows the view identical to that of FIG. 7 which is the explanatory view of the fifth embodiment because FIG. 12 does not illustrate the polarization filter. Similarly, the arrangement corresponding to FIG. 8 which is the explanatory view of the sixth embodiment can be realized using a plurality of plain-shaped polarization filters.

Tenth Embodiment

Figure 13:
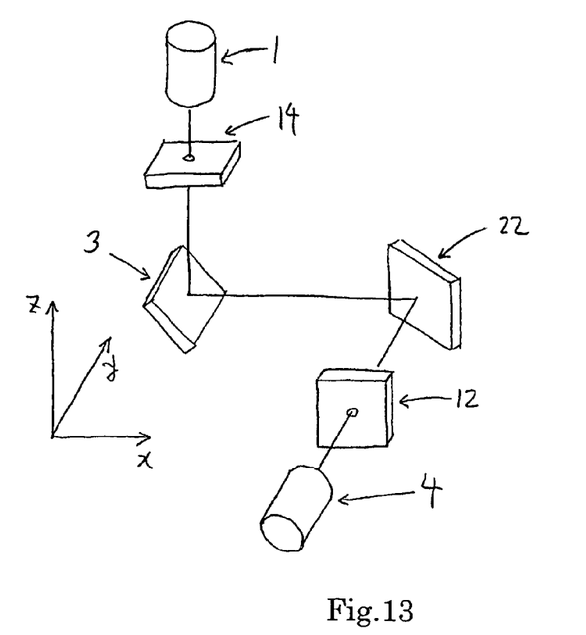
FIG. 13 is a view for showing a tenth embodiment of a fluorescent X-ray analysis apparatus according to the present invention.

FIG. 13 is a view for showing a tenth embodiment of a fluorescent X-ray analysis apparatus according to the present invention and shows a method for measuring a fluorescent X-ray, which has been Compton-scattered by the polarization filter. FIG. 13 is different from the explanatory view of the first embodiment, namely, FIG. 3 in using a polarization filter 22 made of graphite and being provided with the collimator 14 for controlling spread of the angle of the X-ray. When the fluorescent X-ray is scattered by the polarization filter, Rayleigh scattering that the X-ray is scattered while keeping the energy and Compton scattering that the X-ray is scattered with small energy lost occur and in this case, depending on a filter material, a phenomenon such that the intensity of Compton scattering is made larger than the intensity of Rayleigth scattering dozens of times has been found. For this purpose, as a material of the polarization filter, a material made of a light element such as graphite and plastic or the like is profitable. In other words, it is preferable that the polarization filter constituting the tenth embodiment is made of a material of a major ingredient, of which atomic number is 14 or less, such as aluminum and quarts ($SiO_2$) or the like, or a material of a major ingredient, of which atomic number is 8 or less, such as plastic ($C_xO_yH_z$) or the like.

As Compton scattering intensity in a normal fluorescent X-ray analysis, mainly, Compton scattering of a property X-ray based on a tube target material of the X-ray tube in the sample is mainly considered, so that analysis using this is not considered. However, according to the constitution that an optical element (a polarization filter) is disposed at a rear step of the sample like the present invention, Compton scattering is generated for all fluorescent X-rays emitted by the element in the sample and this makes it possible to analyze the X-ray using a Compton scattering peak in place of or in addition to analysis using the fluorescent X-ray itself. However, the Compton scattering peak found by the normal fluorescent X-ray analysis is thicker than the fluorescent X-ray peak and its resolution is not good, so that the Compton scattering peak itself has a low utility value because the X-rays which are Compton-scattered in the sample are detected in a wide angle range.

However, according to the present invention using a polarization system, since the X-ray satisfying a scatter angle of 90 degrees in the sample and the polarization filter is only used, a collimator or the like is disposed on its light path to measure the fluorescent X-ray while controlling spread of an angle. Accordingly, depending on the constitution of the apparatus, it is possible to make a peak width of Compton scattering to be observed equal to a peak width of the fluorescent X-ray and analysis of the X-ray only using the Compton scattering peak or analysis of the X-ray jointly using the Compton scattering peak becomes possible. Depending on the constitution of the apparatus and a measurement condition, by enhancing a use efficiency of the X-ray by controlling spread of the scatter angle, a method to sharpen the Compton scattering peak and decrease its background at the same time becomes possible.

Figure 14A:
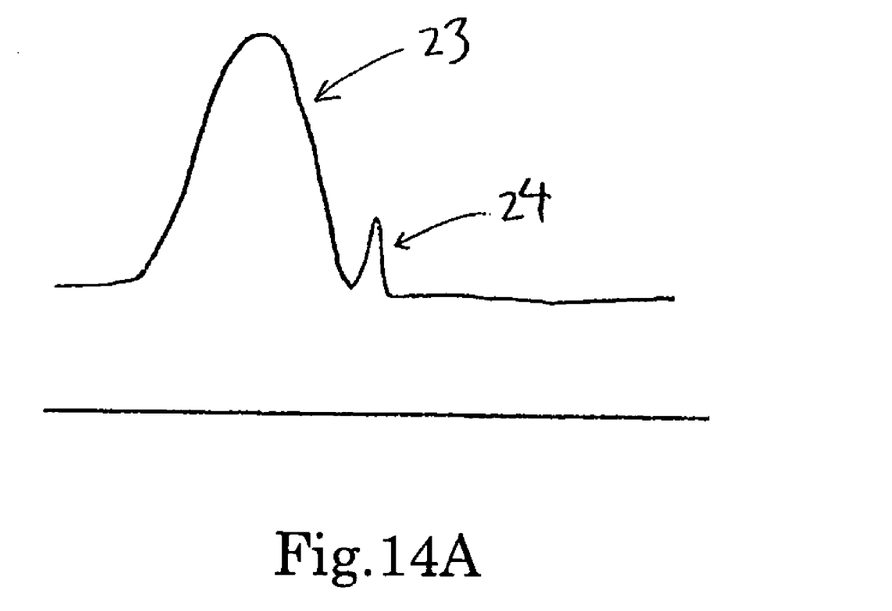
FIGS. 14A and 14B are views for explaining a measurement spectrum according to the tenth embodiment of a fluorescent X-ray analysis apparatus according to the present invention.
Figure 14B:
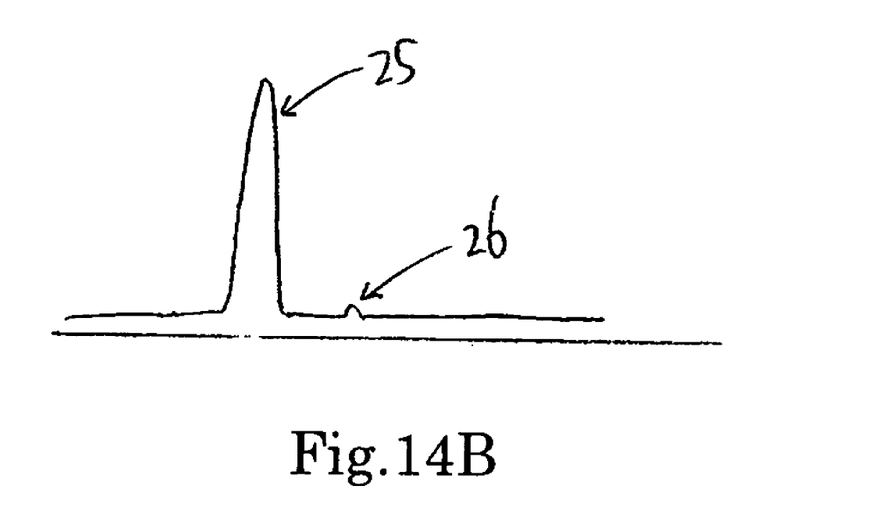

FIG. 14A shows a Compton scattering peak 23 and a fluorescent X-ray peak 24, which are observed in a normal fluorescent X-ray analysis. FIG. 14B shows a Compton scattering peak 25 and a fluorescent X-ray peak 26, which are observed in the case that the same spectrum is measured while controlling spread of the scatter angle. With reference to these drawings, the manner that the background is decreased by controlling spread of the scatter angle and the fluorescent X-ray peak is also decreased at the same time has been found. In addition, with respect to the Compton scatter peak, it has been found that its area is decreased but its shape is sharpened.

Eleventh Embodiment

Figure 15:
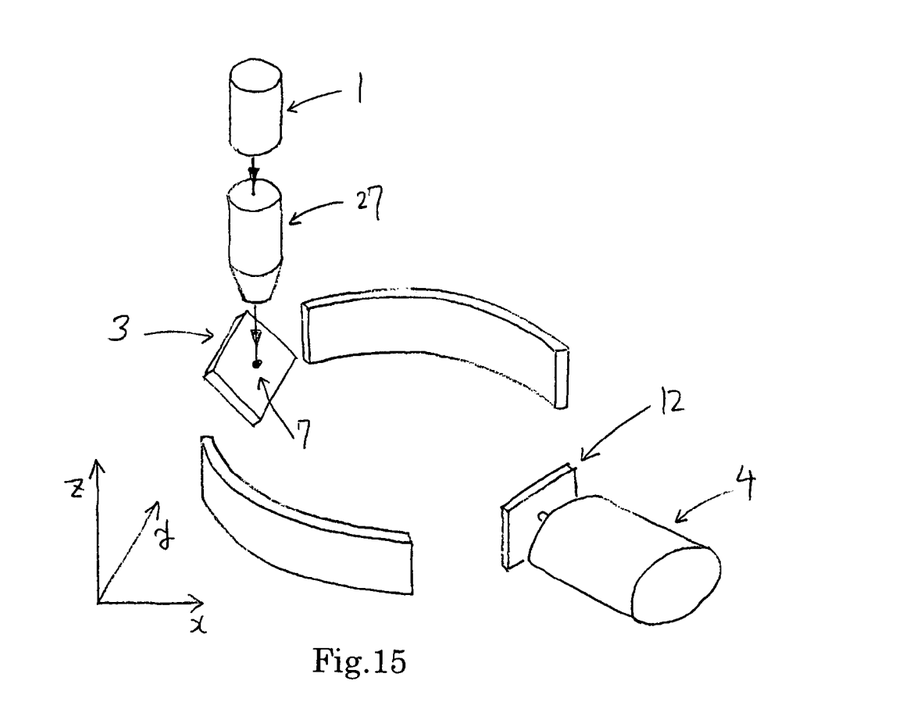
FIG. 15 is a view for showing an eleventh embodiment of a fluorescent X-ray analysis apparatus according to the present invention.
Figure 16:
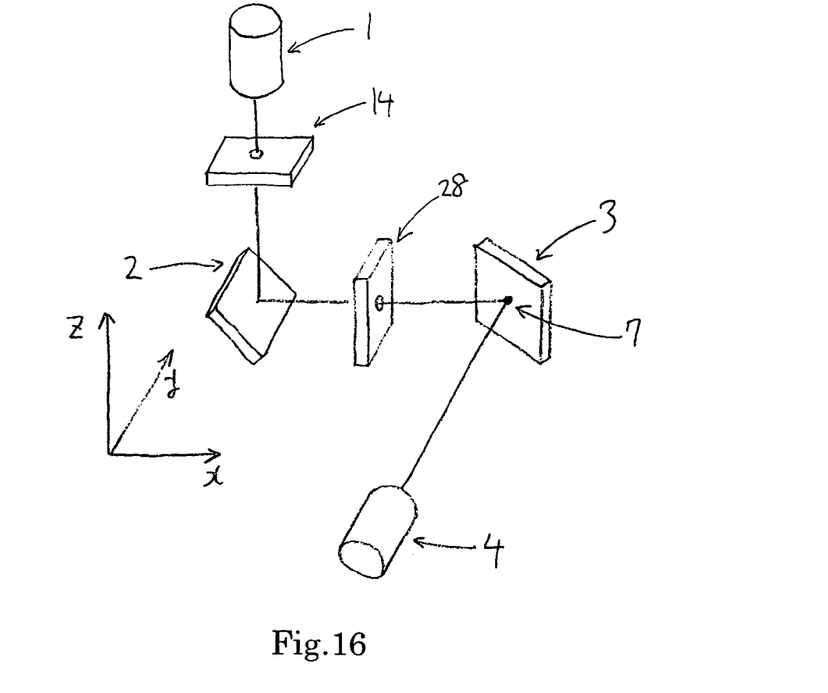
FIG. 16 is a view for showing an arrangement for analysis of a minute portion in a conventional fluorescent X-ray analysis apparatus.

FIG. 15 is a view showing the eleventh embodiment of the fluorescent X-ray analysis apparatus according to the present invention and shows the constitution of the apparatus in the case of carrying out the analysis of the minute portion. On the other hand, FIG. 16, which is an explanatory view of a conventional example, shows a method to carry out the analysis of the minute portion in the normal constitution of the apparatus. In FIG. 16, the lens for the X-ray cannot be used in front of the sample in order to keep the polarization condition, so that an excitation range on the sample 3 is controlled by using the collimator 28. As a result, the X-ray capable of being used for exciting the sample is remarkably reduced and the measurement efficiency is also deteriorated. On the other hand, FIG. 15, which is an explanatory view of the first embodiment, shows a manner that a lens for an X-ray 27 to focus the X-rays from the X-ray tube 1 is disposed between the X-ray tube 1 and the sample 3, the X-ray in its light path has both of the polarization conditions in two directions, and the lens for the X-ray 27 can be used without problems because it is not necessary to save the polarization conditions. Accordingly, according to the constitution of the apparatus of the present invention, the analysis of the minute portion can be carried out without deterioration of efficiency.

What is claimed is:

1. A fluorescent X-ray analysis apparatus, comprising:
an X-ray tube for generating an X-ray;
a sample support portion for supporting a sample receiving the X-ray;
a polarization filter for receiving an X-ray to be generated from the sample receiving the X-ray; and
a detector for detecting the X-ray from the polarization filter;
wherein the X-ray tube, the sample support portion, the polarization filter, and the detector are arranged so that three light paths, namely, a light path from the X-ray tube to the sample, a light path from the sample to the polarization filter, and a light path from the polarization filter to the detector intersect with each other at 90 degrees.

2. The fluorescent X-ray analysis apparatus according to claim 1, wherein a filter having a light receiving surface for receiving the X-ray from the sample curved toward the side of the sample is used as the polarization filter.

3. The fluorescent X-ray analysis apparatus according to claim 2, wherein, as the shape of the polarization filter, the light receiving surface is curved so as to be along a circumference of one circle, the sample, and the detector, or a detector collimator are arranged so as to be separated 180 degrees on the circumference, and the X-ray tube is disposed so that the direction of the X-ray from the X-ray tube toward the sample is vertical to the surface made by the circle.

4. The fluorescent X-ray analysis apparatus according to claim 3, wherein, as a shape of the polarization, which is curved so as to be along the circumference, a part of a shape so as to adhere to a columnar surface is used.

5. The fluorescent X-ray analysis apparatus according to claim 2, wherein an X-ray generation source of the X-ray tube and the detector or the detector collimator are arranged so as to be separated 180 degrees on a sphere; a plurality of polarization filters curved so as to be along circumferences of plural circles having a smaller diameter than a diameter of the sphere is arranged on the sphere passing through the position of the detector or the position of the detector collimator, and the sample is arranged on the circumference separated from the detector or the detector collimator 180 degrees for the plural circles.

6. The fluorescent X-ray analysis apparatus according to claim 5, wherein the sample, the X-ray generation source, and the detector or the detector collimator, which are arranged on the circumferences of the above-described plural circles, are aligned so as to be aligned on a circumference of other circle.

7. The fluorescent X-ray analysis apparatus according to claim 1, wherein, as the polarization filter, a plurality of plain-shaped polarization filters is arranged so that light receiving surfaces of them are located along a circumference of one circle; the sample, and the detector or the detector collimator are arranged so as to be separated 180 degrees on the circumference; and the X-ray tube is disposed so that the direction of the X-ray from the X-ray tube toward the sample is vertical to the surface made by the circle.

8. The fluorescent X-ray analysis apparatus according to claim 7, wherein the plurality of plain-shaped polarization filters is aligned so as to contact a columnar surface.

9. The fluorescent X-ray analysis apparatus according to claim 1, wherein an X-ray generation source of the X-ray tube and the detector or the detector collimator are arranged so as to be separated 180 degrees on a sphere; a plurality of plain-shaped polarization filters so as to be along circumferences of plural circles having a smaller diameter than a diameter of the sphere is arranged on the sphere passing through the position of the detector or the position of the detector collimator, and the sample is arranged on the circumference separated from the detector or the detector collimator 180 degrees for the plural circles.

10. The fluorescent X-ray analysis apparatus according to claim 9, wherein the sample, the X-ray generation source, and the detector or the detector collimator, which are arranged on the circumferences of the above-described plural circles, are aligned so as to be aligned on a circumference of other circle.

11. The fluorescent X-ray analysis apparatus according to claim 1, comprising measurement means for measuring a component after the fluorescent X-ray generated in the sample is Compton-scattered by the polarization filter.

12. The fluorescent X-ray analysis apparatus according to claim 11, wherein the polarization filter is made of a material of a major ingredient, of which atomic number is 14 or less.

13. The fluorescent X-ray analysis apparatus according to claim 12, wherein the polarization filter is made of a material of a major ingredient, of which atomic number is 8 or less.

14. The fluorescent X-ray analysis apparatus according to claim 1, wherein a lens for an X-ray for focusing the X-rays from the X-ray tube is arranged between the X-ray tube and the sample.

15. A fluorescent X-ray analysis method for arranging an X-ray tube, a sample, a polarization filter, and a detector so that three light paths, namely, an X-ray light path from the X-ray tube to the sample, an X-ray light path from the sample to the polarization filter, and an X-ray light path from the polarization filter to the detector intersect with each other at 90 degrees.

16. The fluorescent X-ray analysis method according to claim 15, wherein a component after the fluorescent X-ray generated in the sample is Compton-scattered by the polarization filter is measured.

17. A fluorescent X-ray analysis apparatus comprising:
an X-ray source configured to irradiate an X-ray;
a sample interrogated by the X-ray from the X-ray source to thereby excite a fluorescent X-ray out therefrom;
a polarization filter configured to reflectively extract the fluorescent X-ray from the sample; and
a detector configured to detect the fluorescent X-ray reflected from the polarization filter, wherein the X-ray source, the sample and the polarization filter are so arranged as to present at least one X-ray path which perpendicularly breaks at each of the sample and the polarization filter.

18. A fluorescent X-ray apparatus according to claim 17, wherein the polarization filter comprises at least one curved reflective surface.

19. A fluorescent X-ray apparatus according to claim 17, wherein the polarization filter comprises at least one planar reflective surface.

20. A florescent X-ray apparatus according to claim 17, wherein the polarization filter comprises a reflective surface which constitutes at least part of a circle, and the sample and the detector are located at the ends of a diameter of the circle.

21. A florescent X-ray apparatus according to claim 20, further comprising a shield located at the center of the circle to shield the X-ray from the X-ray source from directly irradiating the detector.

22. A fluorescent X-ray apparatus according to claim 17, wherein the sample and the detector are arranged at the ends of a diameter of an imaginary circle, and the polarization filter comprises at least one reflective surface which constitutes at least part of each of at least one arc tangential to the imaginary circle at the detector.

23. A fluorescent X-ray apparatus according to claim 22, wherein the at least one arc is arranged along a large arc which passes at the sample and the detector.

24. A fluorescent X-ray apparatus according to claim 8, wherein the at least one planar surface is arranged along a circle, and the sample and the detector are arranged at the ends of a diameter of the circle.

* * * * *